(12) United States Patent
Groszmann

(10) Patent No.: US 8,886,289 B2
(45) Date of Patent: Nov. 11, 2014

(54) DYNAMIC REFERENCE METHOD AND SYSTEM FOR USE WITH SURGICAL PROCEDURES

(75) Inventor: Daniel Eduardo Groszmann, Cambridge, MA (US)

(73) Assignee: General Electric Company, Schenectady, NY (US)

( * ) Notice: Subject to any disclaimer, the term of this patent is extended or adjusted under 35 U.S.C. 154(b) by 432 days.

(21) Appl. No.: 13/223,021

(22) Filed: Aug. 31, 2011

(65) Prior Publication Data

US 2011/0319751 A1    Dec. 29, 2011

Related U.S. Application Data

(63) Continuation of application No. 11/809,093, filed on May 31, 2007, now Pat. No. 8,024,026.

(51) Int. Cl.
*A61B 5/05*   (2006.01)

(52) U.S. Cl.
USPC ........... 600/424; 600/410; 600/414; 600/425; 600/426; 600/427

(58) Field of Classification Search
None
See application file for complete search history.

(56) References Cited

U.S. PATENT DOCUMENTS

| | | | | |
|---|---|---|---|---|
| 4,054,881 A * | 10/1977 | Raab | | 342/448 |
| 4,109,199 A * | 8/1978 | Ball et al. | | 324/202 |
| 4,531,526 A * | 7/1985 | Genest | | 600/300 |
| 4,613,866 A * | 9/1986 | Blood | | 342/448 |
| 4,642,786 A * | 2/1987 | Hansen | | 702/153 |
| 4,737,794 A * | 4/1988 | Jones | | 342/448 |
| 4,742,356 A * | 5/1988 | Kuipers | | 342/448 |
| 5,287,273 A * | 2/1994 | Kupfer et al. | | 600/431 |
| 5,307,072 A * | 4/1994 | Jones, Jr. | | 342/147 |
| 5,453,686 A * | 9/1995 | Anderson | | 324/207.17 |
| 6,032,530 A * | 3/2000 | Hock | | 73/379.01 |
| 6,177,792 B1 * | 1/2001 | Govari et al. | | 324/207.12 |
| 6,314,312 B1 * | 11/2001 | Wessels et al. | | 600/427 |
| 6,615,155 B2 * | 9/2003 | Gilboa | | 702/150 |
| 6,980,921 B2 * | 12/2005 | Anderson et al. | | 702/150 |
| 7,006,858 B2 * | 2/2006 | Silver et al. | | 600/345 |
| 7,158,754 B2 * | 1/2007 | Anderson | | 455/41.1 |
| 7,181,261 B2 * | 2/2007 | Silver et al. | | 600/345 |
| 7,675,394 B2 * | 3/2010 | Fujimori et al. | | 335/151 |
| 7,686,757 B2 * | 3/2010 | Minai | | 600/12 |
| 7,794,407 B2 * | 9/2010 | Rothenberg | | 600/508 |
| 7,798,958 B2 * | 9/2010 | Kawano et al. | | 600/118 |
| 7,834,621 B2 * | 11/2010 | Anderson | | 324/300 |
| 7,902,817 B2 * | 3/2011 | Anderson | | 324/207.17 |

(Continued)

OTHER PUBLICATIONS

Faris et al, Novel Technique for Cardiac Electromechanical Mapping with Magnetic Resonance Imaging Tagging and an Epicardial Electrode Sock, Annals of Biomedical Engineering, vol. 31, pp. 430-440, 2003.

*Primary Examiner* — Long Le
*Assistant Examiner* — Nicholas Evoy
(74) *Attorney, Agent, or Firm* — Fletcher Yoder, P.C.

(57) ABSTRACT

A substrate configured for placement on an internal organ or internal tissue is provided. In certain embodiments, the substrate conforms to and moves with the internal organ or internal tissue. Three or more sensor elements are integrated on the substrate. In one implementation, the substrate and associated sensor elements provide dynamic referencing of the internal organ or internal tissue after registration of the sensor data with images and/or volumetric representations of the internal organ or internal tissue.

15 Claims, 5 Drawing Sheets

(56) References Cited

U.S. PATENT DOCUMENTS

| | | | |
|---|---|---|---|
| 8,197,494 B2 * | 6/2012 | Jaggi et al. | 606/130 |
| 8,249,689 B2 * | 8/2012 | Anderson | 600/424 |
| 8,388,546 B2 * | 3/2013 | Rothenberg | 600/508 |
| 8,512,256 B2 * | 8/2013 | Rothenberg | 600/508 |
| 2001/0047133 A1 * | 11/2001 | Gilboa et al. | 600/429 |
| 2003/0163287 A1 * | 8/2003 | Vock et al. | 702/187 |
| 2003/0220557 A1 | 11/2003 | Cleary et al. | |
| 2004/0082842 A1 * | 4/2004 | Lumba et al. | 600/338 |
| 2004/0107070 A1 * | 6/2004 | Anderson et al. | 702/150 |
| 2004/0129279 A1 | 7/2004 | Fabian et al. | |
| 2004/0236192 A1 * | 11/2004 | Necola Shehada et al. | 600/301 |
| 2004/0254419 A1 * | 12/2004 | Wang et al. | 600/8 |
| 2004/0260346 A1 | 12/2004 | Overall et al. | |
| 2005/0049486 A1 * | 3/2005 | Urquhart et al. | 600/429 |
| 2005/0065433 A1 * | 3/2005 | Anderson | 600/424 |
| 2005/0084147 A1 | 4/2005 | Groszmann | |
| 2005/0085720 A1 * | 4/2005 | Jascob et al. | 600/424 |
| 2005/0107687 A1 * | 5/2005 | Anderson | 600/424 |
| 2005/0169510 A1 | 8/2005 | Zuhars et al. | |
| 2006/0039591 A1 | 2/2006 | Zettel et al. | |
| 2006/0253032 A1 | 11/2006 | Altmann et al. | |
| 2007/0208542 A1 * | 9/2007 | Vock et al. | 702/187 |
| 2007/0238988 A1 * | 10/2007 | Minai | 600/424 |
| 2008/0133171 A1 * | 6/2008 | Feichtinger et al. | 702/141 |
| 2010/0016661 A1 * | 1/2010 | Nagase et al. | 600/109 |
| 2010/0037902 A1 * | 2/2010 | Wirtz et al. | 128/899 |
| 2010/0121150 A1 * | 5/2010 | Fujimori et al. | 600/118 |
| 2010/0160732 A1 * | 6/2010 | Minai | 600/117 |
| 2010/0168516 A1 * | 7/2010 | Uchiyama | 600/109 |
| 2010/0204566 A1 * | 8/2010 | Uchiyama et al. | 600/424 |

* cited by examiner

DYNAMIC REFERENCE METHOD AND SYSTEM FOR USE WITH SURGICAL PROCEDURES

CROSS-REFERENCE TO RELATED APPLICATIONS

This application is a continuation of U.S. patent application Ser. No. 11/809,093, entitled "Dynamic Reference Method and System for Use With Surgical Procedures," filed May 31, 2007, which is herein incorporated by reference in its entirety for all purposes.

BACKGROUND

The present technique relates generally to invasive procedures, such as surgical procedures. In particular, the present technique relates to image-guided surgery employing various radiological modalities.

As medical imaging technologies have matured, it has become possible to combine the use of medical imaging techniques with the performance of invasive procedures. For example, invasive procedures, such as certain surgical procedures, may benefit from the use of imaging techniques that allow a clinician to visualize the internal or obscured structures in the surgical area while the procedure is being performed. In this way, the clinician may perform the desired surgical procedure with a greater chance of success and without unnecessary tissue damage.

In practice, such image-guided surgical techniques typically employ a tracking frame of reference device placed proximate to the anatomy of interest. The reference device moves with the patient to provide accurate and consistent tracking of the anatomy of interest. Typically, the reference device needs to be rigidly secured to the anatomy of interest. As a result, the reference device is generally attached to hard bone near the anatomy of interest. As a result, such image-guided surgical techniques are generally limited to regions in the body bounded by bony anatomy, such as cranial neurosurgery, spine, orthopedic, and sinus procedures.

While such techniques are useful, clearly there are other areas of the body that are not bounded by bony structures and that might also benefit from such image-guided techniques. However, regions of the body that are not bounded by such bony structures, such as cardiac and abdominal regions, currently cannot benefit from such image-guided techniques due to the inability to affix a reference device proximate to the anatomy of interest. Further, many internal organs that might benefit from image-guided surgical techniques can move, such as due to respiration, gravity, and so forth, and therefore, present additional interventional challenges. In addition, even in regions of the anatomy where there is proximate bone, it may not be desirable to attach a reference device to the bone. Therefore, it is desirable to provide a reference technique for image-guided surgical procedures that does not require a reference device affixed to skeletal structures.

BRIEF DESCRIPTION

The present technique is generally directed to the dynamic referencing of an internal organ or tissue in an image-guided invasive procedure. In one implementation, a substrate having three or more sensor elements is provided. In such an embodiment, the substrate is placed on an internal organ, such as during a surgical open or laparoscopic procedure. Signals or fields generated by the sensor elements, such as electromagnetic signals or fields, may be used to determine the positions of the sensor elements. The positions of the sensor elements may then be registered with a set of image based data which may or may not include image data representative of the sensor elements. In one embodiment, the registration occurs automatically. Once the signals generated by the sensor elements is registered with the images or volumetric representations of the internal organ, the position and orientation information derived from the sensor elements may be used to modify or adjust the visual representation of the internal organ to reflect motion or deformation of the organ. The modified or adjusted visual representation may then be used to allow a surgeon or other clinician to perform an image-guided invasive procedure based on images reflecting the current position and shape of the internal organ.

In accordance with one aspect of the present technique, a surgical reference system is provided. The surgical reference system includes a substrate configured for placement on an internal organ or tissue such that the substrate conforms to and moves with the internal organ or tissue. Three or more sensor elements are integrated on the substrate.

In accordance with a further aspect of the present technique, a method for tracking dynamic motion of an organ is provided. The method includes the act of generating a first set of position data for three or more sensor components integrated on a substrate placed on an internal organ. The first set of position data is based on signals or fields generated by the sensor components. A second set of position data is generated for the three or more sensor components based on an identification of the three or more sensor components in one or more radiological images or volumetric representations of the internal organ. Corresponding sensor components are identified in the first set of position data and the second set of position data. The first set of position data is registered with the one or more radiological images or volumetric representations based on the identification of corresponding sensor components in the first set of position data and the second set of position data.

In accordance with an additional aspect of the present technique, a method for tracking dynamic motion of an organ is provided. The method includes the act of generating position and orientation data for one or more sensor components provided on a substrate placed on an internal organ. The position and orientation data is based on signals or fields generated by the sensor components. A shape model of the substrate is generated based on the position and orientation data. In addition, a region of interest in one or more radiological images or volumetric representations is segmented. The region of interest comprises at least one of the internal organ, a portion of the internal organ, or a region proximate or connected to the internal organ. A shape model of the region of interest is generated based on the segmentation. The shape model of the substrate and the shape model of the region of interest are registered.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present technique is directed to dynamic referencing of internal organs for image-guided surgical procedures. In particular, the present technique utilizes a conformable member or substrate, such as gauze or a biocompatible plastic, configured with one or more tracking devices. The conformable substrate is configured for placement on or near an internal organ of interest such that movement of the organ can be tracked in conjunction with acquired images or image data. In particular, in an exemplary embodiment, the movement of the tracking devices is automatically registered with the image data, without the use of anatomical or fiducial markers. In this manner, an image-guided surgical procedure may be performed using the dynamic reference information acquired using the substrate. Because the substrate can be associated with the anatomy of interest without being affixed to bone, the present technique may be suitable for use with percutaneous procedures performed on internal organs that may move or be moved and which are not close to a suitable skeletal anchor. Examples of such organs include, but are not limited to the liver, lungs, kidneys, pancreas, bladder, and so forth.

Figure 1:
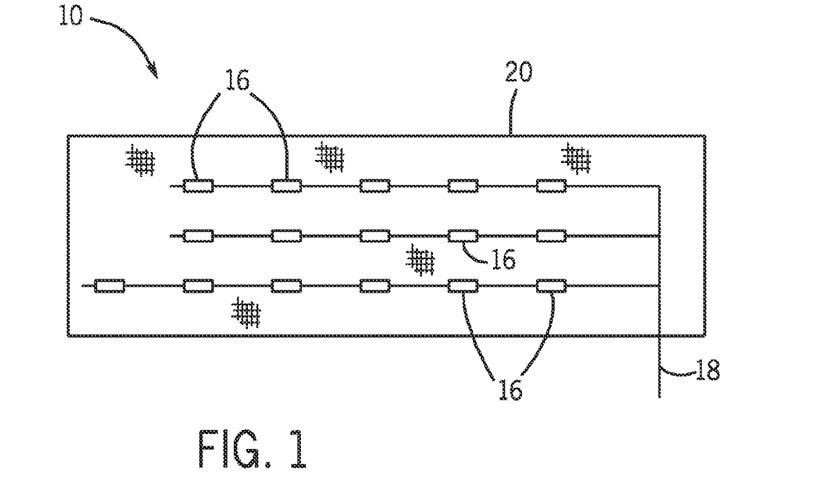
FIG. 1 depicts a piece of surgical gauze including sensor components, in accordance with an exemplary embodiment of the present technique.

For example, referring to FIG. 1, a biocompatible substrate 10 is depicted that is suitable for placement near or on an organ of interest. In an exemplary embodiment, the substrate 10 is a conformable piece of surgical gauze 20 which may be of any suitable dimensions or shape. The substrate 10 is provided with three or more sensor elements 16 that, in an exemplary embodiment, may be used to acquire position information relating to the substrate 10. Indeed, in certain exemplary embodiments it may be desirable to include more than three sensor elements 16 because the number of sensor elements 16 will generally provide more points defining the surface of an organ on which the substrate is placed. In other words, the number of sensor elements 16 provided on the substrate 10 is generally proportional to the level of surface or conformational detail provided by the substrate 10 when placed on an organ.

In the depicted embodiment, a conductive element 18 is also provided which may be suitable for providing power to the sensor elements 16 in implementations in which the sensor elements are powered. In one implementation, where the substrate 10 is a piece of surgical gauze, the conductive element 18 may be run through the blue tail commonly found on surgical gauze. In such embodiments, the blue tail, may be impregnated with barium so that the gauze is easily located using X-ray based imaging techniques.

Figure 2:
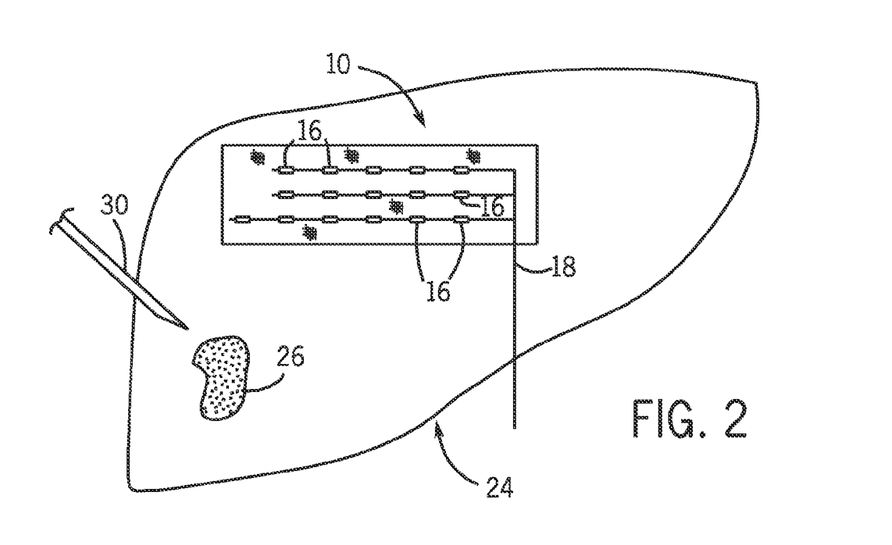
FIG. 2 depicts a piece of surgical gauze including sensor components placed on an organ, in accordance with an exemplary embodiment of the present technique.

The exemplary substrate 10 is depicted placed on an internal organ 24 (here depicted as a liver) in FIG. 2. The substrate 10 may be placed on the internal organ 24 as part of an open surgical procedure in which the internal organ 24 is exposed. Alternatively, the substrate 10 may be placed on the internal organ 24 using laparoscopic surgical techniques utilizing a small incision. For example, in such laparscopic implementations, the substrate 10 may be introduced through a small incision in a rolled or folded form, maneuvered to the internal organ site, and unrolled or unfolded on or near the internal organ 24 using laparoscopic techniques. For example, laparoscopic delivery may be accomplished using a suitable catheter for delivery of a piece of gauze 20.

In an exemplary embodiment, the substrate 10, regardless of how it is placed on or near the internal organ 24, conforms to the shape of the internal organ 24 at the location where the substrate 10 overlays the internal organ 24. For example, the substrate 10, in one embodiment, may be a piece of surgical gauze 20 that adheres to the internal organ 24 due to the surface tension of fluids on the surface of the internal organ 24. Such adhesion may be enhanced or improved by the addition of saline or other suitable fluids to the surface of the internal organ 24. In embodiments where the substrate 10 is conformable, such as where the substrate 10 is a piece of gauze 20, the shape assumed by the conformable substrate 10 generally corresponds to the corresponding surface of the internal organ at that location. Further, in such an implementation, the conformable substrate 10 may be placed on an area of the internal organ 24 having sufficient curvature such that the area may be uniquely identified by the sensor elements 16, as discussed below.

In exemplary implementations in which the internal organ 24 (such as the depicted liver) moves essentially as a rigid body during respiration, the substrate 10 placed on or near the internal organ 24 will move with the internal organ 24. Further, to the extent that the substrate 10 conforms to the internal organ 24, the substrate 10 will reflect conformational changes in the internal organ 24, i.e., if the internal organ changes shape, the substrate 10 will conform to the internal organ 24 and will, therefore, deform to the new shape of the internal organ 24. Because the substrate 10 will move with and conform to the internal organ 24, the substrate 10 can act as a dynamic reference with regard to the internal organ 24. As a result, a surgical procedure, such as surgical removal (such as with a tracked needle 30) of a lesion 26 using laparoscopic or open techniques, can be performed using image-guided navigation using position or motion information obtained using the sensor elements 16 integrated on the substrate 10.

Typically, the sensor elements 16 are not provided in a linear or symmetric arrangement, i.e., the sensor elements 16 do not form a single line, such that the respective sensor elements 16 can be distinguished from one another based upon their known spatial relationships. For example, in the exemplary depicted embodiments of FIGS. 1 and 2, the sensor elements 16 are provided in a 3×5 array such that the totality of information received from the sensor elements 16 can be used to distinguish the respective sensor elements 16 from one another.

In one embodiment, the sensor elements 16 are provided as electromagnetic (EM) microsensors that are integrated into or securely attached to the substrate 10. Such EM microsensors may be provided as either hollow or solid sensor coils which generate EM fields. Exemplary solid EM coils may be about 0.75 mm in diameter (or greater) and about 2 mm long (or greater). Likewise, exemplary hollow EM coils may be about 2 mm in diameter (or greater) and about 2 mm long (or greater). Such solid or hollow EM coils can provide a spatial tracking accuracy having less than about 1 mm root mean square (RMS) error. Further each sensor coil can be tracked in position with this accuracy over a volume sufficient for the image-guided procedures described herein, i.e., within the field of view of a medical imaging system.

In implementations employing such EM coils, each EM sensor coil can provide information regarding the orientation of the respective coil in two directions. In one embodiment, however, a single coil cannot provide sufficient information to determine the roll of the respective coil since the coils are axisymmetric. Therefore, each coil, in such an embodiment, has five degrees of freedom. If at least two such coils are combined into or integrated onto a device, such as the substrate 10, so that the coils have a known and fixed relationship to one another, then six degrees of freedom (x, y, z, roll, pitch, yaw) can be determined from the aggregate or combined information obtained form the two or more coils. In this way, the EM fields generated by the EM coils may be used to determine the position and orientation of the substrate 10 upon which they are integrated. For example, in the embodiment depicted in FIGS. 1 and 2, the sensor elements 16 (which are presumed to be EM coils in this example) that are fixed on the substrate 10 allow the position, orientation, and conformation (i.e., shape) of the substrate 10 to be determined based upon the EM fields generated by the EM coils.

As described above, a substrate 10 may be used accordance with the present technique to allow image-guided invasive procedures. As will be appreciated, any imaging modality suitable for use in an image-guided surgical procedure may be employed in the present technique. Examples of such imaging modalities include X-ray based imaging techniques which utilize the differential attenuation of X-rays to generate images (such as three-dimensional fluoroscopy, computed tomography (CT), tomosynthesis techniques, and other X-ray based imaging technologies). Other exemplary imaging modalities suitable for image-guided surgical procedures may include magnetic resonance imaging (MRI), ultrasound or thermoacoustic imaging techniques, and/or optical imaging techniques. Likewise, nuclear medicine imaging techniques (such as positron emission tomography (PET) or single positron emission computed tomography (SPECT)) that utilize radiopharmaceuticals may also be suitable imaging technologies for performing image-guided surgical procedures. Likewise, combined imaging modality systems, such as PET/CT systems, may also be suitable for performing image-guided surgical procedures as described herein. Therefore, throughout the present discussion, it should be borne in mind that the present techniques are generally independent of the system or modality used to acquire the image data. That is, the technique may operate on stored raw, processed or partially processed image data from any suitable source.

Figure 3:
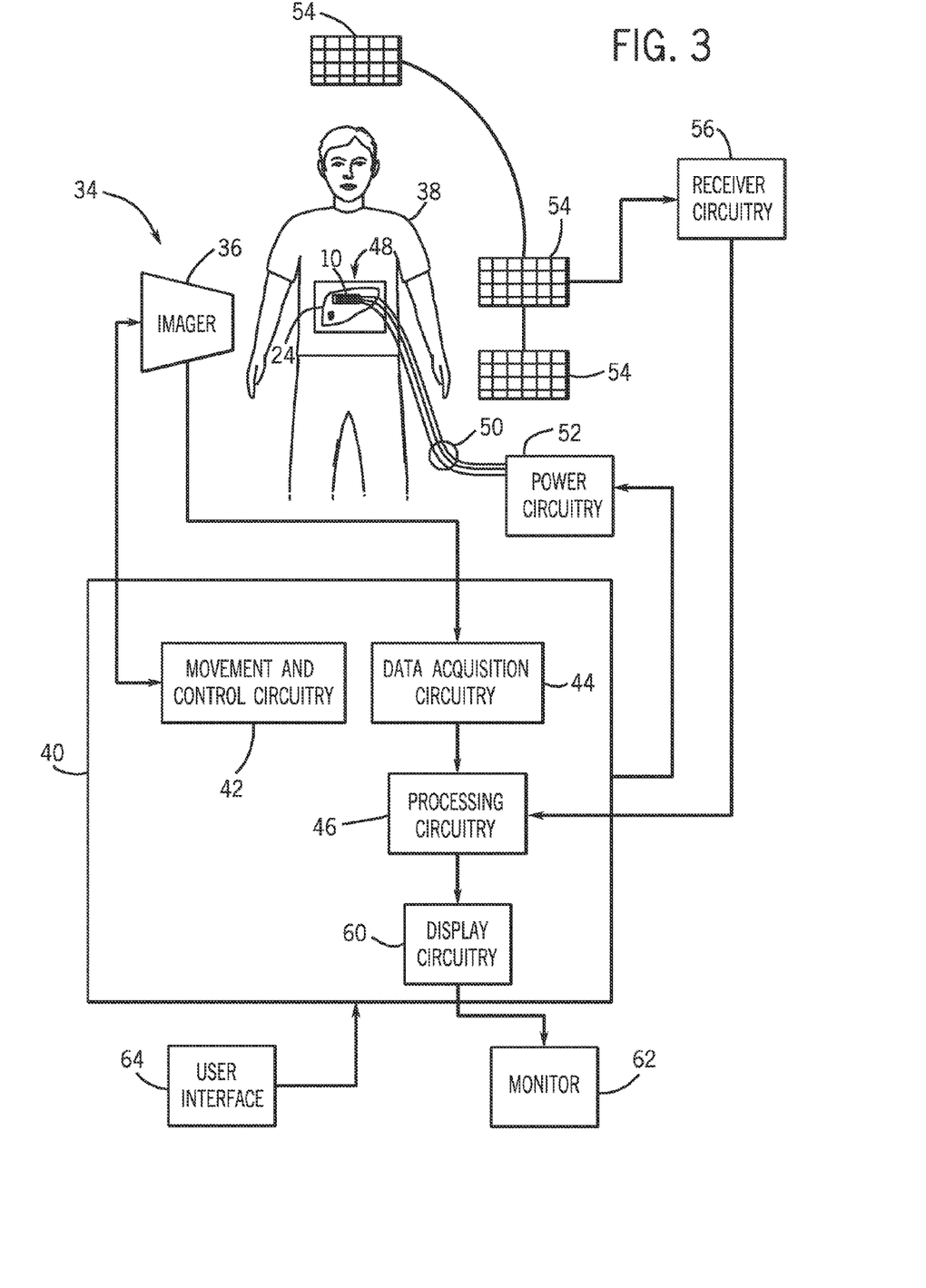
FIG. 3 depicts exemplary components of an imaging system and a position determining system, in accordance with an exemplary embodiment of the present technique.

For example, turning now to FIG. 3, an overview of an exemplary generalized imaging system 34, which may be representative of various imaging modalities, is depicted. The generalized imaging system 34 typically includes some type of imager 36 which detects signals and converts the signals to useful data. As described more fully below, the imager 36 may operate in accordance with various physical principles for creating the image data. In general, however, image data indicative of regions of interest in a patient 38 are created by the imager 36 in a digital medium for use in image-guided surgical procedures.

The imager 36 may be operated by system control circuitry 40 which controls various aspects of the imager operation and acquisition and processing of the image data as well as dynamic reference data acquired using the present techniques. In the depicted generalized embodiment, the system control circuitry 40 includes movement and control circuitry 42 useful in operating the imager 36. For example, the movement and control circuitry 42 may include radiation source control circuits, timing circuits, circuits for coordinating the relative motion of the imager 36 (such as with regard to a patient support and/or detector assembly), and so forth. The imager 36, following acquisition of the image data or signals, may process the signals, such as for conversion to digital values, and forwards the image data to data acquisition circuitry 44. For digital systems, the data acquisition circuitry 44 may perform a wide range of initial processing functions, such as adjustment of digital dynamic ranges, smoothing or sharpening of data, as well as compiling of data streams and files, where desired. The data are then transferred to data processing circuitry 46 where additional processing and analysis are performed. For the various digital imaging systems available, the data processing circuitry 46 may perform substantial reconstruction and/or analyses of data, ordering of data, sharpening, smoothing, feature recognition, and so forth.

In addition to processing the image data, the processing circuitry 46 may also receive and process motion or location information related to an anatomical region of interest, such as the depicted internal organ 24 and/or lesion 26 which are accessible via an open surgical incision 48 or a laparoscopic surgical entry. In the depicted embodiment, a substrate 10 is placed on the internal organ 24 (here depicted as the liver of the patient 38). The substrate 10, as discussed above, is provided with numerous (for example, three or more) sensor elements 16 (see FIGS. 1 and 2) configured to provide position information. In an exemplary embodiment, the sensor elements 16 are EM coils each configured to generate a distinctive and distinguishable EM field. In certain embodiments where the sensor elements 16 are powered, the sensor elements 16 may be connected, such as via one or more conductive wires 50, to suitable power circuitry 52, such as an electrical power source or outlet or a suitable battery. While in the depicted embodiment the power circuitry 52 is depicted as being separate from the system control circuitry 40, in other embodiments the power circuitry 52 may be part of the system control circuitry 40.

In the depicted embodiment, the signals or fields generated by the sensor elements 16 are detected by one or more antennas 54. The detected location information is provided to or acquired by receiver circuitry 56 which in turn provides the location data to the processing circuitry 46. As discussed in greater detail below, the location data may be used in conjunction with the image data to facilitate an image-guided procedure. In another embodiment, the antennas 54 are used for transmission instead of detection, i.e., the antennas 54 are transmitters, and generate EM fields which are detected by the sensors elements 16. In either embodiment, location information can be determined in sufficient detail to allow the motion and/or configuration of the organ to be tracked.

The processed image data and/or location data may be forward to display circuitry 60 for display at a monitor 62 for viewing and analysis. While operations may be performed on the image data prior to viewing, the monitor 62 is at some point useful for viewing reconstructed images derived from the image data collected. The images may also be stored in short or long-term storage devices which may be local to the imaging system 34, such as within the system control circuitry 40, or remote from the imaging system 34, such as in picture archiving communication systems. The image data can also be transferred to remote locations, such as via a network.

For simplicity, certain of the circuitry discussed above, such as the movement and control circuitry 42, the data acquisition circuitry 44, the processing circuitry 46, and the display circuitry 60, are depicted and discussed as being part of the system control circuitry 40. Such a depiction and discussion is for the purpose of illustration only, however, and is intended to merely exemplify one possible arrangement of this circuitry in a manner that is readily understandable. Those skilled in the art will readily appreciate that in other embodiments the depicted circuitry may be provided in different arrangements and/or locations. For example, certain circuits may be provided in different processor-based systems or workstations or as integral to different structures, such as imaging workstations, system control panels, and so forth, which functionally communicate to accomplish the techniques described herein.

The operation of the imaging system 34 may be controlled by an operator via a user interface 52 which may include various user input device, such as a mouse, keyboard, touch screen, and so forth. Such a user interface may be configured to provide inputs and commands to the system control circuitry 40, as depicted. Moreover, it should also be noted that more than a single user interface 52 may be provided. Accordingly, an imaging scanner or station may include an interface which permits regulation of the parameters involved in the image data acquisition procedure, whereas a different user interface may be provided for manipulating, enhancing, and viewing resulting reconstructed images.

Figure 4:
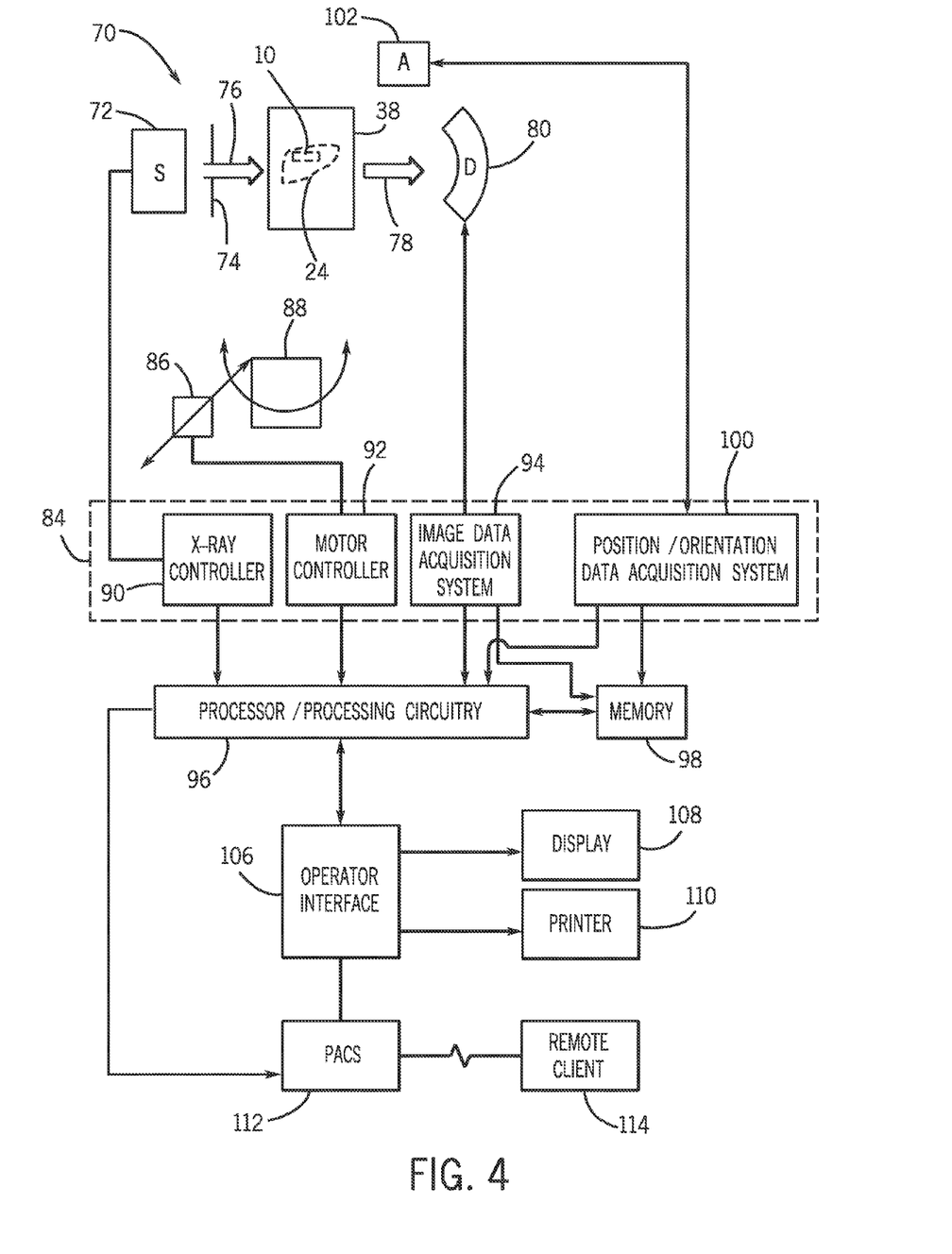
FIG. 4 depicts exemplary components of a computed tomography or three-dimensional fluoroscopy imaging system and a position determining system, in accordance with an exemplary embodiment of the present technique.

To discuss the technique in greater detail, a specific medical imaging modality based generally upon the overall system architecture outlined in FIG. 3 is depicted in FIG. 4, which generally represents an X-ray based system 70. It should be noted that, while reference is made in FIG. 4 to an X-ray based system, the present technique also encompasses other imaging modalities, as discussed above, such as MRI, PET, SPECT, ultrasound, and so forth.

In the depicted exemplary embodiment, FIG. 4 illustrates diagrammatically an X-ray based imaging system 70 for acquiring and processing image data. In the illustrated embodiment, imaging system 70 is a computed tomography (CT) system or three-dimensional fluoroscopy imaging system designed to acquire X-ray projection data, to reconstruct the projection data into a two or three-dimensional image, and to process the image for display and analysis in accordance with the present technique. In the embodiment illustrated in FIG. 4, X-ray based imaging system 70 includes a source of X-ray radiation 72 positioned adjacent to a collimator 74. The X-ray source 72 may be a standard X-ray tube or one or more solid-sate X-ray emitters.

In the depicted embodiment, the collimator 74 permits a stream of radiation 76 to pass into a region in which a subject, such as the patient 38 is positioned. The stream of radiation 76 may be generally fan or cone shaped, depending on the configuration of the detector array as well as the desired method of data acquisition. A portion of the radiation 78 passes through or around the patent 38 and impacts a detector array, represented generally as reference numeral 80. Detector elements of the array produce electrical signals that represent the intensity of the incident X-ray beam. The signals generated by the detector array 80 may be subsequently processed to reconstruct a visual representation (i.e., an image or volumetric representation) of the features within the patient 38. For example, images of the internal organ 24 may be reconstructed in the depicted embodiment.

A variety of configurations of the detector 80 may be employed in conjunction with the techniques described herein. For example, the detector 80 may be a multi-row detector, such as a detector having eight or sixteen rows of detector elements, which achieves limited longitudinal coverage of the object or patient being scanned. Similarly, the detector 80 may be an area detector, such as a high-resolution radiographic detector having hundreds of rows of detector elements, which allows positioning of the entire object or organ being imaged within the field of view of the system 70. Regardless of the configuration, the detector 80 enables acquisition and/or measurement of the data used in image reconstruction of the internal organ 24.

The source 72 is controlled by a system controller 84, which furnishes both power, and control signals for examination procedures. Moreover, the detector 80 is coupled to the system controller 84, which commands acquisition of the signals generated in the detector 80. The system controller 84 may also execute various signal processing and filtration functions, such as for initial adjustment of dynamic ranges, interleaving of digital image data, and so forth. In general, system controller 84 commands operation of the imaging system 70 to execute examination protocols and to process acquired data. In the present context, system controller 84 also includes signal processing circuitry, typically based upon a general purpose or application-specific digital computer, associated memory circuitry for storing programs and routines executed by the computer (such as programs and routines for implementing the present technique), as well as configuration parameters and image data, interface circuits, and so forth.

In the embodiment illustrated in FIG. 4, the system controller 84 is coupled to a linear positioning subsystem 86 and rotational subsystem 88. The rotational subsystem 88 enables the X-ray source 72, collimator 74 and the detector 80 to be rotated one or multiple turns around the patient 38. It should be noted that the rotational subsystem 88 might include a gantry or C-arm apparatus. Thus, the system controller 84 may be utilized to operate the gantry or C-arm. The linear positioning subsystem 86 typically enables a patient support, such as a table, upon which the patient rests, to be displaced linearly. Thus, the patient table may be linearly moved relative to the gantry or C-arm to generate images of particular areas of the patient 38.

Additionally, as will be appreciated by those skilled in the art, the source 72 of radiation may be controlled by an X-ray controller 90 disposed within the system controller 84. Particularly, the X-ray controller 90 may be configured to provide power and timing signals to the X-ray source 72. A motor controller 92 may also be part of the system controller 84 and may be utilized to control the movement of the rotational subsystem 88 and the linear positioning subsystem 86.

Further, the system controller 84 is also illustrated as including an image data acquisition system 94. In this exemplary embodiment, the detector 80 is coupled to the system controller 84, and more particularly to the image data acquisition system 94. The image data acquisition system 94 receives data collected by readout electronics of the detector 80. The image data acquisition system 94 typically receives sampled analog signals from the detector 90 and converts the data to digital signals for subsequent processing by processing circuitry 96, which may, for example, be one or more processors of a general or application specific computer.

As depicted, the system controller 84 also includes a position/orientation data acquisition system 100 configured to acquire position and orientation data from one or more antennas 102. In the depicted embodiment, the one or more antennas 102 detect signals and/or fields generated by sensor elements 16 on a substrate 10 placed on the internal organ 24 undergoing imaging. The position/orientation data acquisition system 100 processes signals acquired from the antennas 102 to generate position and/or orientation information about the substrate 10 which is representative of the internal organ 24. The position and/or orientation information generated by the position/orientation data acquisition system 100 may be provided to the processing circuitry 96 and/or a memory 98 for subsequent processing.

The processing circuitry 96 is typically coupled to the system controller 84. The data collected by the image data acquisition system 94 and/or by the position/orientation data acquisition system 100 may be transmitted to the processing circuitry 96 for subsequent processing and visual reconstruction. The processing circuitry 96 may include (or may communicate with) a memory 98 that can store data processed by the processing circuitry 96 or data to be processed by the processing circuitry 96. It should be understood that any type of computer accessible memory device capable of storing the desired amount of data and/or code may be utilized by such an exemplary system 70. Moreover, the memory 98 may include one or more memory devices, such as magnetic or optical devices, of similar or different types, which may be local and/or remote to the system 70. The memory 98 may store data, processing parameters, and/or computer programs having one or more routines for performing the processes described herein.

The processing circuitry 96 may be adapted to control features enabled by the system controller 84, i.e., scanning operations and data acquisition. For example, the processing circuitry 96 may be configured to receive commands and scanning parameters from an operator via an operator interface 106 typically equipped with a keyboard and other input devices (not shown). An operator may thereby control the system 70 via the input devices. A display 108 coupled to the operator interface 106 may be utilized to observe a reconstructed visual representation. Additionally, the reconstructed image may also be printed by a printer 110, which may be coupled to the operator interface 106. As will be appreciated, one or more operator interfaces 106 may be linked to the system 70 for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

The processing circuitry 96 may also be coupled to a picture archiving and communications system (PACS) 112. Image data generated or processed by the processing circuitry 96 may be transmitted to and stored at the PACS 112 for subsequent processing or review. It should be noted that PACS 112 might be coupled to a remote client 114, radiology department information system (RIS), hospital information system (HIS) or to an internal or external network, so that others at different locations may gain access to the image data.

The systems and devices described above may be utilized, as described herein, to provide dynamic referencing for a region of a patient undergoing an invasive procedure, such as a surgical open or laparoscopic procedure. In an exemplary embodiment, dynamically acquired position and orientation data for the region of the patient may be acquired using the substrate 10 and the associated sensor elements 16 and the data may be automatically registered with concurrently or previously acquired image data without the use of anatomical or fiducial markers. In this way, the surgical procedure may be performed or guided based upon the dynamically referenced visual representation.

Figure 5:
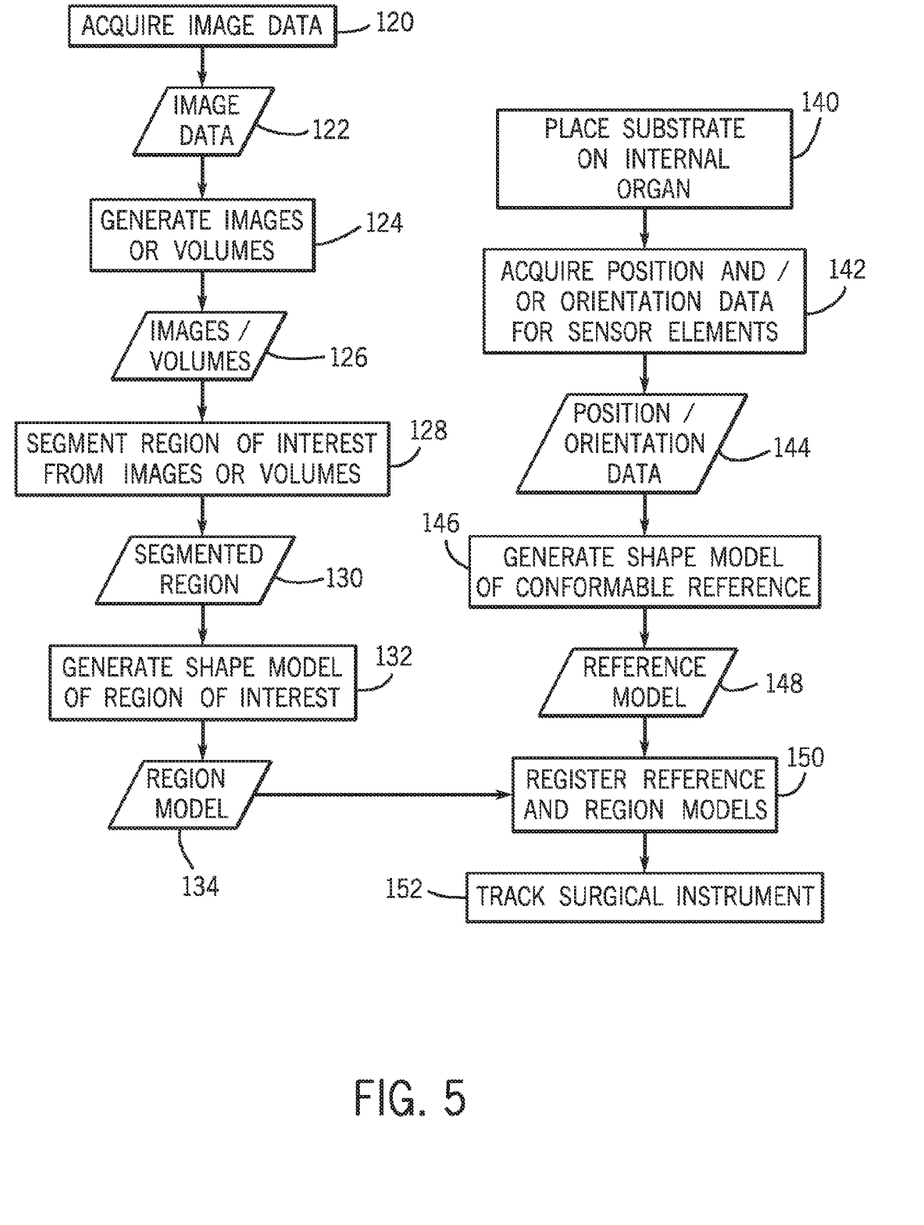
FIG. 5 depicts exemplary acts for using a position determining system, in accordance with an exemplary embodiment of the present technique.

For example, referring to FIG. 5, exemplary acts corresponding to one implementation of the present technique are provided. In the implementation depicted in FIG. 5, the image data 122 is acquired (Block 120) prior to the invasive procedure. As noted above, the image data 122 may be acquired using one or more suitable imaging modalities, such as three-dimensional fluoroscopy, CT, MRI, and so forth. In the depicted embodiment, the image data 122 is used to generate (Block 124) one or more visual representations, such as images or volumes 126, of the internal organ 24 (see FIG. 2) or region of interest.

The images or volumes 126 are segmented (Block 128) in the depicted implementation to provide one or more segmented regions 130. Such a segmentation process typically identifies pixels or those portions of an image representing common structures, such as organs or tissues. For example, a segmentation a process may identify surfaces or boundaries defining an organ or tissue (such as by changes in intensity or some other threshold criteria). In this way, all of those pixels representing respective organs or tissues, portions of such organs or tissues, or regions proximate or connected to such organs or tissues may be identified and distinguished from one another, allowing processing or evaluation of only the portions of an image associated with the organs or tissues of interest.

The images or volumes 126 may be segmented using known segmentation techniques, such as intensity and/or volume thresholding, connectivity clustering, and so forth. In one embodiment, the segmentation allows the organ, tissue or region of interest to be geometrically modeled. In an exemplary embodiment, the segmented region corresponds to the internal organ 24 or other structure upon which the substrate 10 (see FIGS. 1 and 2) will be placed for dynamic referencing. While the depicted actions describe an embodiment in which images or volume 126 generated from the acquired image data 122 are segmented, in other embodiments the segmentation may be performed on the image data 122 itself, with the segmented image data being subsequently used to generate images or volume of the internal organ 24 or region of interest. Based upon the segmented image or volume of the internal organ, i.e., the segmented region 130, a model 134 of the region is generated (Block 132) which generally corresponds to the internal organ 24 or other region of interest as determinable form the imaging process.

In some embodiments, the region model 134 may incorporate image data acquired using more than one type of imaging modality. For example, in some embodiments, it may be desirable to use image data derived form both an MRI system and an X-ray based imaging system, such as a three-dimensional fluoroscopy system. In such an embodiment, the signals acquired by both system may be registered, as discussed below, such that the combined images and/or volumes 126, segmented region 130 and/or region model 134 consists of or is representative of the image information acquired by each imaging modality.

During the invasive procedure performed on the internal organ 24 (or other region of interest), the substrate 10 is placed (Block 140) on the internal organ 24. As noted above, the substrate 10 includes at least three sensor elements 16. The sensor elements 16 generate respective signals (such as respective EM fields) which may be acquired (Block 142) or measured to derive position and/or orientation data 144 for each respective sensor element 16. The position and/or orientation data 144 may be used to generate (Block 146) a reference model 148 representing the surface of the internal organ 24.

The reference model 148 derived from the position and/or orientation data 144 is registered (block 150) with the region model 134 generated using the imaging process. In an exemplary embodiment, the registration of the reference model 148 and the region model 134 is accomplished automatically, such as using iterative closest point techniques. In this manner, the sensor elements 16 of the substrate 10 are automatically registered to the surface of the internal organ 24, such as the liver. As will be appreciated, the more sensor elements 16 present on the substrate 10, the more robust and accurate the automatic registration process will be. Further, in embodiments in which the sensor elements 16 are integrated on a substrate 10 that conforms to the internal organ 24, soft tissue deformation of the internal organ 24 may be captured by the sensor elements 16 as the substrate 10 conforms to accommodate motion or deformation of the internal organ 24. In such an embodiment, a deformable registration process may be employed to find correspondences between the sensor elements 16 on the moving or deforming internal organ 24 and the corresponding images or volumes. In other words, a deformable registration process may be employed to allow the sensor elements 16 to be registered to the corresponding images or volumes even though the internal organ 24 may have moved or may be shaped slightly differently between the time the image data 122 was acquired and the time the position and/or orientation data 144 was acquired.

An image-guided invasive procedure may be performed using the registered reference model 148 (based on the position and/or orientation data) and region model 134 (based on the image data). In particular, once the previously acquired image-based information or model is registered to the measured position and/or orientation data, changes in the position and/or orientation data can be used to visually indicate changes to the image-based model. In other words, a displayed image of the internal organ 24 may be updated, modified, altered, or otherwise, changed, based on the most current position and/or orientation data obtained from the sensor elements 16 placed on the internal organ 24. In this way, even though no imaging processes are occurring during the operation, the previously acquired image data can be updated and manipulated to provide an accurate and current representation of the internal organ (or other internal region) undergoing the procedure.

Based on this registration between the region model 134 (derived the image data) and reference model 148 (derived from the sensor element data), a surgical instrument may be tracked (Block 152) during an invasive procedure, such as a surgical open or laparoscopic procedure. Examples of such surgical instruments that may be tracked include biopsy needles, catheters, ablation needles, forceps, and so forth. Typically the surgical instrument being tracked also includes a sensor element 16, such as an EM sensor, so that position and/or orientation information for the surgical instrument is also acquired, thereby allowing the position of the surgical instrument to be displayed in conjunction with the registered image of the moving and/or deformed internal organ 24. In this manner, a system such as those described herein, may display to a user in real-time or substantially real-time the location of the surgical device relative to the moving and/or deformed internal organ 24.

While the preceding described an implementation in which the imaging procedure is performed prior to the surgical procedure, in other implementations the imaging procedure is performed concurrently with the surgical procedure. For example, referring to FIG. 6, acts associated with a further exemplary embodiment of the present technique are depicted. In this embodiment, the sensor elements 16 integrated on a substrate 10 are placed on the internal organ 24 of interest, such as via an open surgical or laparoscopic procedure. Position and/or orientation data 158 is acquired (Block 156) for the sensor elements 16 placed on the surface of the internal organ 24. For example, in embodiments where the sensor elements 16 generate EM signals or fields, these signals or fields can be detected and/or measured, such as using one or more antenna arrays as described above, to derive a position and/or orientation for each respective sensor element 16.

Figure 6:
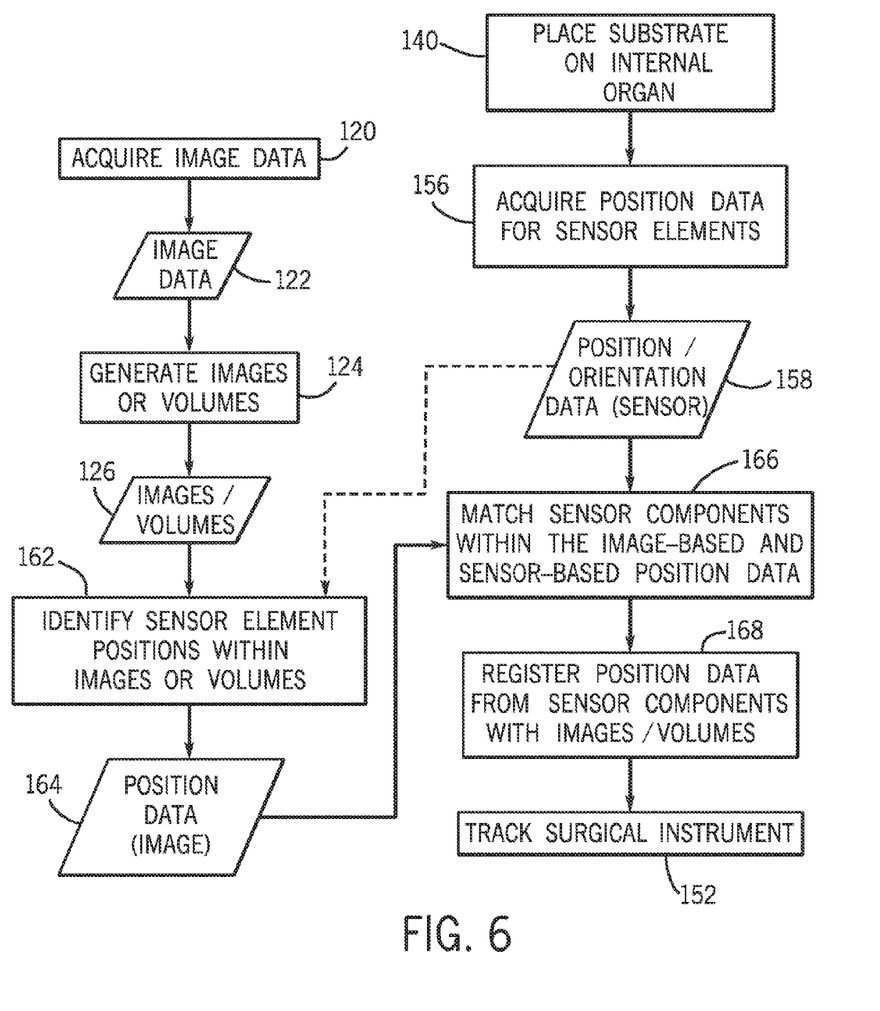
FIG. 6 depicts exemplary acts for using a position determining system, in accordance with a further exemplary embodiment of the present technique.

In the depicted embodiment, image data 122 is acquired (Block 120) and is used to generate (Block 124) one or more images and/or volumes 126. Some or all of the sensor elements 16 are located (Block 162) in the images and/or volumes 126 such that the position data 164 for the respective sensor elements 16 is obtained with respect to the images/volumes 126. In an exemplary embodiment, the sensor elements 16 are automatically located in the images/volumes 126. For example, the sensor elements 16 may be automatically located using image processing techniques such as intensity and/or volume thresholding, connectivity clustering, template matching, and so forth. In addition, in some embodiments, the positions of the sensor elements 16 are known with respect to one another based on the measured signals or fields generated by the sensor elements 16. This sensor derived position data 158 may be used to find the sensor elements 16 in the images and/or volumes 126.

Once some or all of the sensor elements 16 are identified in the images and/or volumes, the positions 164 of the sensor elements 16 located in the images and/or volumes may be matched (Block 166) to the corresponding sensor element locations as determined from the sensor position data 158. In other words, the sensor elements 16 located in the images and/or volumes are matched with the corresponding sensor elements signals and/or fields generated by the sensor elements 16. In one embodiment, this may be facilitated by using a non-symmetric pattern of sensor elements 16 on the substrate 10. Alternatively, a sufficiently large number (i.e., four or more) of sensor elements 16 may be provided in one embodiment such that all possible matches may be permuted and the match generating the smallest registration error is selected as the correct match or correspondence.

Based on the established or possible correspondences, the sensor element positions derived using the sensor data and the imaging data are registered (Block 168). As noted above, in some embodiments, the registration and the establishment of the correspondences may actually depend on one another, i.e., the registration errors associated with different possible matches may be used to select the correct correspondence. In one embodiment the centroid of each sensor element 16 as determined in the images and/or volumes is registered to the corresponding sensor element signal in the position data derived from the sensor elements 16. In certain implementations the registration can be accomplished using iterative optimization techniques or a closed form solution. As noted above, in certain embodiments, to obtain a unique registration it is generally desired that the three or more sensor elements not lie on or near a straight line.

Once the sensor elements 16 are registered in both the sensor space (such as EM space) and the image space, the interventional procedure may be performed using the dynamic tracking of the internal organ based upon the signals from the sensor elements 16. For example, no further imaging may be performed or the image data may be updated only sporadically, with other updates to the images used in the interventional procedure being based upon the continuous, substantially real-time tracking of the sensor elements 16. In this way, even though imaging does not occur or occurs only sporadically during the operation, the displayed images can be updated and manipulated to provide an accurate and current representation of the internal organ 24 (or other internal region) undergoing the procedure.

In one implementation a surgical instrument may be tracked (Block 152) during an invasive procedure, such as a surgical open or laparoscopic procedure, using images updated based upon the position data derived form the sensor elements and the registration of these signals with the image and/or volumes 126. Examples of such surgical instruments that may be tracked include biopsy needles, catheters, ablation needles, forceps, and so forth. Typically the surgical instrument being tracked also includes a sensor element 16, such as an EM sensor, so that position and/or orientation information for the surgical instrument is also acquired, thereby allowing the position of the surgical instrument to be displayed in conjunction with the image updated using the position data for the sensor elements 16. In this manner, a system such as those described herein, may display to a user in real-time or substantially real-time the location of the surgical instrument relative to the moving and/or deformed internal organ 24.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A surgical reference system, comprising:
a substrate that conforms to and moves with an internal organ or internal tissue when placed thereon;
three or more sensor elements each generating x, y, and z coordinate information and integrated on the substrate, wherein the sensor elements generate one or both of positional or directional signals when in use; and
a power supply electrically connected to the three or more sensor elements.

2. The surgical reference system of claim 1, wherein the substrate comprises surgical gauze.

3. The surgical reference system of claim 1, wherein the three or more sensor elements comprise three or more electromagnetic sensor coils.

4. The surgical reference system of claim 1, comprising one or more receiving components configured to detect the positional or directional signals generated by the three or more sensor elements.

5. The surgical reference system of claim 1, comprising one or more antennas configured to detect electromagnetic fields generated by the three or more sensor elements.

6. The surgical reference system of claim 1, comprising one or more transmitters configured to generate electromagnetic fields detectable by the three or more sensor elements.

7. The surgical reference system of claim 1, wherein the three or more sensor elements allow tracking of the substrate.

8. The surgical reference system of claim 1, wherein each sensor element provides position information in three dimensions and two or more of roll, pitch, or yaw.

9. The surgical reference system of claim 1, wherein the three or more sensor elements in combination provide position information in three dimensions and roll, pitch, and yaw information.

10. A surgical reference system, comprising:
a substrate that conforms to and moves with an internal organ or internal tissue when placed thereon;
three or more sensor elements each generating x, y, and z coordinate information and integrated on the substrate, wherein the sensor elements generate one or both of positional or directional data when in use;
a power supply electrically connected to the three or more sensor elements; and
a registration module configured to register image data generated by an imaging system with the positional or directional data generated by the three or more sensor elements without use of a fixed reference system.

11. The surgical reference system of claim 10, wherein the registration module is configured to register image data with the positional or directional data without use of an anatomical or fiducial marker.

12. The surgical reference system of claim 10, wherein the registration module is configured to provide the registered image data and positional or directional data to be used during an image-guided surgical procedure.

13. The surgical reference system of claim 10, wherein the registration module is configured to provide the registered image data and positional or directional data to be used to track a surgical instrument during an invasive surgical procedure.

14. The surgical reference system of claim 13, wherein the surgical instrument comprises an instrument sensor element, wherein the instrument sensor element generates positional or directional signals when in use.

15. The surgical reference system of claim 1, wherein the three or more sensor elements are arranged as an array on the substrate.

* * * * *